United States Patent [19]

Knorr et al.

[11] Patent Number: 5,656,482
[45] Date of Patent: Aug. 12, 1997

[54] RAPID GERMINATION OF ORCHID SEEDS FROM IMMATURE CAPSULES

[75] Inventors: Dietrich W. Knorr, Newark; Lynn G. Romagnoli, Greenville, both of Del.; Cheryl P. Stevens, West Grove, Pa.

[73] Assignee: University of Delaware, Newark, Del.

[21] Appl. No.: 169,640

[22] Filed: Mar. 17, 1988

[51] Int. Cl.⁶ .............................. A01H 4/00; C12N 5/04; A01C 1/02; A01C 1/06
[52] U.S. Cl. .................. 435/410; 435/420; 435/430; 800/200; 800/DIG. 62; 47/57.6; 47/58
[58] Field of Search .................... 435/240.4, 240.45; 800/200, DIG. 62; 47/57.6, 58

[56] References Cited

PUBLICATIONS

L. Knudson, "Germination of Seeds of Vanilla," Am. Jour. Bot. 37:241–247 (1950).
C. P. Hegarty, "Observations on the Germination of Orchid Seed," Am. Orchid Soc. Bull. 24:457–464 (1955).
C. L. Withner, "Ovule Culture and Growth of Vanilla Seedlings," Am. Orchid Soc. Bull. 24:380–382 (1955).
Sahai et al., "Producing high value food ingredients via plant biotechnology," The World Biotech Report 1986, Part 1, pp.71–85.
Hughes, KW (1981) in BV Conger, ed., Cloning Agricultural Plants via In Vitro Techniques, CRC Press, Inc., Boca Raton, Fla., pp. 11–13 and 21–22.
Flores et al. (1981) in K Maramowsch, ed, Advances in Cell Culture, vol. 1, Academic Press, Inc., NY, p. 249.
Shoemaker et al. (1986) Plant Cell Rep. 3:178–181.
Salisbury et al. (1985) Plant Physiology, third ed., Wadsworth Publ. Co., Belmont, CA, p. 419.
An Rao (1977) in J. Reinert et al., eds., Plant Cell, Tissue, and Organ Culture, Springer–Verlag, NY, pp. 44 and 53–55.
Olgamborg (1984) in IK Vasil, ed., Cell Culture and Somatic Cell Genetics of Plants, vol. 1, Academic Press, Inc., NY, p. 22.
RT Northern (1970) Home Orchid Growing, 3rd ed., Van Nostrand Reinhold, Co., NY, p. 108.

*Primary Examiner*—David T. Fox
*Attorney, Agent, or Firm*—Huntley & Associates

[57] ABSTRACT

Seeds of the vanilla orchid *Vanilla planifolia* attached to an explant of the seed pod are germinated and incubated in a culture medium containing growth regulators.

5 Claims, No Drawings

RAPID GERMINATION OF ORCHID SEEDS FROM IMMATURE CAPSULES

BACKGROUND OF THE INVENTION

1. Field of the Invention

This invention relates to, and has its principal object provision of, the rapid germination of orchid seeds from green capsules, particularly the seeds of the commercially important orchid *Vanilla planifolia*.

2. Prior Art

Representative art published on the germination of *Vanilla planifolia* seeds includes:

L. Knudson, "Germination of seeds of vanilla," Am. Jour. Bot. 37:241–247 (1950);

C. P. Hegarty, "Observations on the germination of orchid seed," Am. Orchid Soc. Bull. 24:457–464 (1955); and C. L. Withner, "Ovule culture and growth of vanilla seedlings," Am. Orchid Soc. Bull. 24:380–382 (1955).

See also, Sahai et al., "Producing high value food ingredients via plant biotechnology," The World Biotech Report 1980, Part 1, pp. 71–85.

SUMMARY OF THE INVENTION

In accordance with the present invention, rapid germination of seeds of an orchid, *Vanilla planifolia*, is obtained from the green capsule by a process comprising:

(1) aseptic preparation of explants of capsule tissue, with seeds adhering, from the green capsule; followed by (2) incubation of the explants at around 25° C. and in darkness in an agar-solidified culture medium of Murashige and Skoog (MS) basal salts supplemented with specific and novel growth regulators, vitamins, sucrose, and casein hydrolysate.

DETAILED DESCRIPTION OF INVENTION

In this process, decontamination of the green seed pod or capsule from fungi and microorganisms is carried out, for example, in CLOROX, and repeated after about twenty-four hours. Explants with seeds adhering are then prepared from the decontaminated seed pod and placed in the culture medium.

A commercial preparation of MS basal salts (Hazleton Research Products, Lenexa, Kans.) was used in the culture medium. The salts are described by Murashige and Skoog, "A revised medium for rapid growth and bioassays with tobacco tissue cultures," Physiol Plant. 15:473–497(1962), and consist of the following:

| Commercial Aqueous MS Basal Salt Solution Without Agar | |
|---|---|
| Component | mg/liter |
| $NH_4NO_3$ | 1650.00 |
| $KNO_3$ | 1900.000 |
| $CaCl_2$(Anhydrous) | 333.000 |
| $MgSO_4$(Anhydrous) | 181.000 |
| $KH_2PO_4$ | 170.000 |
| FeNaEDTA | 36.700 |
| $H_3BO_3$ | 6.200 |
| $MnSO_4.H_2O$ | 16.900 |
| $ZnSO_4.7H_2O$ | 8.600 |
| KI | .830 |
| $Na_2MoO_4.2H_2O$ | 2.500 |
| $CuSO_4.5H_2O$ | .025 |
| $CoCl_2.6H_2O$ | .025 |
| Total | 4303.530 mg/l |

Here an aqueous solution of the basal salts at pH 5.0–5.8 is supplemented with:

| Component | g(or mg)/l |
|---|---|
| Sucrose | 20–40 |
| Casein hydrolysate | 0–500 (mg/l) |
| Thiamine hydrochloride | 0–10 (mg/l) |
| Myo-inositol | 0–1000 (mg/l) |

Casein (acid) hydrolysate is a commercially available protein derived from cow's milk which has been hydrolyzed with acid. It is an organic source of nitrogen and amino acids and, as used here, has a total nitrogen content of approximately 13.3% with an amino nitrogen content of 10%.

In addition, selected auxins and cytokinins (growth regulators) are also included as supplements. Useful auxins are α-naphthaleneacetic acid and 2,4-dichlorophenoxyacetic acid, each up to about 5 mg/l. A useful cytokinin is 6-benzylaminopurine in a concentration of up to about 1 mg/l. These regulators may be used alone or in admixture.

The aqueous solution of the medium is solidified with 5–15 g/l of agar, 7–9 g/l usually being sufficient.

On the medium just described, *Vanilla planifolia* seeds begin to germinate within thirty-four days of initiation of the process compared to six weeks or up to a year in other processes. The germinated embryos are transplanted to a fresh medium as desired.

EXAMPLE

A. Preparing the Explant

Immature capsules harvested six months after pollination were cleaned with a mild detergent and surface decontaminated for twenty minutes with 50% CLOROX. The capsules were kept under aseptic conditions, and the CLOROX treatment was repeated after twenty-four hours. Discolored portions were excised and discarded, and the exocarp of the remaining portion of the fruits was removed with a sharp scalpel. Transverse slices of approximately 2–5 mm were prepared. These discs (themselves explants) were cut radially into quarters, and the explants, with placental tissue and seeds adhering, were placed on solified aqueous germination media in Petri dishes.

B. Seed Germination

Seed germination was carried out in a supplemented commercial preparation of MS basal salts supplemented with 3% sucrose, 4.0 mg/l of α-naphthaleneacetic acid, 1.0 mg/l of 6-benzylaminopurine, 500 mg/l of casein (acid) hydrolysate (Sigma Chemical Co., St. Louis), 5.0 mg/l of thiamine hydrochloride, and 1,000 mg/l of myo-inositol. The medium was adjusted to pH 5.8 and hardened with 0.7% agar. The cultures were sealed with Parafilm and incubated in the dark at 25° C. The explants were subcultured after 16 days.

C. Growing Plants

Thirty-four days after initiation of the original cultures, embryos of approximately 1–3 mm length were visible growing from the seeds. Microscopic examination of the explants revealed splitting of seed coats with embryos emerging from them. Some protocorms with rhizoids were observed thirty-nine days after culture initiation. Germination of additional seeds continued for more than eight weeks.

After seven weeks in darkness, the developing embryos, still adhering to the explants, were placed in an incubator under constant fluorescent light (4.5 $\mu E/m^2 \cdot sec$) at 25° C. Twelve days later, a total of 65 embryos was counted on four explants on the medium, their length varying in the 1–10 mm range (Table). Their morphology and development were variable as compared to that described by Knudson (op. cit).

These results are summarized in the table which follows:

TABLE

Number and size of Vanilla embryos produced by seed germination, sixty-one days after culture initiation

| Explant No. | Total No. of embryos before transfer | Total No. of embryos transferred to fresh medium | Mean length of transferred embryos (mm) |
|---|---|---|---|
| 1 | 16 | 13 | 3.5 |
| 2 | 18 | 17 | 3.1 |
| 3 | 6 | 6 | 1.8 |
| 4 | 25 | 22 | 2.5 |
| TOTAL | 65 | 58 | |

The embryos at this point are ready to develop into full-grown Vanilla planifolia plants.

Having described our invention, we claim:

1. The process of obtaining rapid germination of seeds of the orchid Vanilla planifolia from the green capsule of the plant which comprises:

a. decontaminating the capsule by surface sterilization from fungi and microorganisms;

b. aseptically preparing explants of capsule tissue with seeds adhering, the explants being about 2–5 mm thick;

c. transplanting the explants to an agar-solidified culture medium of basal salts supplemented with effective amounts of growth regulators, sucrose, and casein hydrolysate; and d. incubating the explants in the culture medium at about 25° C. in darkness until germination occurs.

2. An aseptic explant for the rapid germination of the seeds of the orchid Vanilla planifolia which comprises a slice about 2–5 mm thick of the green seed capsule of the orchid with the seeds adhering, the surface of the capsule having been decontaminated from fungi and microorganisms.

3. The explant of claim 2 wherein the decontamination is accomplished by an effective oxidizing agent.

4. The explant of claim 3 wherein the decontamination is accomplished by CLOROX.

5. The process of claim 1 wherein the growth regulators are selected from at least one member of the group consisting of $\alpha$-naphthaleneacetic acid, 2,4-dichlorophenoxyacetic acid and 6-benzylaminopurine.

* * * * *